United States Patent [19]

Bliem et al.

[11] Patent Number: 5,187,095

[45] Date of Patent: * Feb. 16, 1993

[54] APPARATUS FOR CULTURING ANIMAL CELLS

[75] Inventors: Rudolf F. Bliem, Castro Valley; Robert V. Oakley, Lafayette; Van Taiariol, Redwood City, all of Calif.

[73] Assignee: Baxter International Inc., Deerfield, Ill.

[ * ] Notice: The portion of the term of this patent subsequent to Apr. 7, 2009 has been disclaimed.

[21] Appl. No.: 824,203

[22] Filed: Jan. 22, 1992

Related U.S. Application Data

[62] Division of Ser. No. 286,756, Dec. 19, 1988, Pat. No. 5,102,790.

[51] Int. Cl.$^5$ .............................................. C12M 3/04
[52] U.S. Cl. ...................... 435/285; 435/288; 435/310
[58] Field of Search ............... 435/703, 240.2, 240.23, 435/283, 284, 285, 288, 299, 300, 310, 311, 240.24, 240, 243, 68.1, 813, 819, 286; 210/150, 151, 255, 284, 291–293; 422/188

[56] References Cited

U.S. PATENT DOCUMENTS

| 2,317,449 | 4/1943 | Flock | 422/188 |
|---|---|---|---|
| 2,338,345 | 1/1944 | Mather | 422/188 |
| 2,338,346 | 1/1944 | Mather | 422/188 |
| 4,172,013 | 10/1979 | Skoda et al. | 435/240 |
| 4,180,543 | 12/1979 | Ward | 422/188 |
| 4,343,904 | 8/1982 | Birch et al. | 435/240 |
| 4,377,639 | 3/1983 | Lee | 435/285 |
| 4,661,458 | 4/1987 | Berry et al. | 435/284 |
| 4,789,634 | 12/1988 | Muller et al. | 435/288 |
| 4,833,083 | 5/1989 | Saxena | 435/284 |
| 5,102,790 | 4/1992 | Bliem et al. | 435/70.3 |

FOREIGN PATENT DOCUMENTS

| 0205790 | 12/1986 | European Pat. Off. | 435/284 |
|---|---|---|---|
| 0224734 | 6/1987 | European Pat. Off. | 435/284 |
| 62-11887 | 5/1987 | Japan | 435/284 |
| 8605202 | 9/1986 | PCT Int'l Appl. | 435/284 |
| 0615841 | 2/1980 | Switzerland | 435/288 |
| 1539263 | 1/1979 | United Kingdom | 435/285 |
| 2103239 | 2/1983 | United Kingdom | 435/285 |

OTHER PUBLICATIONS

Glocken, M. W. et al., "Mammalian Cell Culture: Engineering Principles and Scale-Up," 1983.
"The Production and Use of Swine Vesicular Disease Virus from Pig Kidney Manager of Cells," Biotech. & Bioeng., vol. 24, pp. 245–249 (1982), Whiteside et al.
Spier et al., "Typsinization of BHK 21 monolayer cells crown in Tub Large-Scale Unit Process Systems," Biotech. & Bioeng., vol. 19, pp. 1735–1738 (1977).
Spier et al., "The Production of Foot-and-Mouth Disease Virus from BHK 21C13 Cells" Biotech. & Bioeng., vol. 18, pp. 649–657 (1976).

(List continued on next page.)

Primary Examiner—Robert J. Warden
Assistant Examiner—William H. Beisner
Attorney, Agent, or Firm—St. Onge Steward Johnston & Reens

[57] ABSTRACT

An apparatus for the in vitro culture of animal cells to recover secreted proteins of interest therefrom, affording the capability of being readily and predictably scaled up or down to desired protein production rates, comprised of a housed arrangement of culture subunits containing a packed bed of carrier particles, each subunit being fed in parallel from a common culture medium source, and the spent culture fluid from each subunit being directed to a common spent fluid conduit within the housed arrangement. Scale-up or scale-down is effected by addition or subtraction of culture subunits and/or by increase or decrease in carrier particle volume within a subunit while maintaining substantially constant packed bed height.

3 Claims, 10 Drawing Sheets

OTHER PUBLICATIONS

Davis et al., "The Production of Rubella Virus using BHK 21 Cells", Develop. Bio. Standard, vol. 66, pp. 555-558 (1987).

Griffiths et al., "A Comparison of Unit Process Systems for Anchorage Dependent Cells" Develop. Bio. Standard., vol. 66, pp. 331-338 (1987).

Thorton et al., "Production of Herpes Simplex Virus From MRC-5 Cells" Develop. Bio. Standard, vol. 60, pp. 475-481 (1985).

Whiteside et al., "Factors Affecting The Productivity of Glasc Sphere Progagators" Develop. Bio. Standard, vol. 60, pp. 305-311 (1985).

Whiteside et al., "Foot-and-Mouth Disease Virus Production" Develop. Bio. Standard., vol. 46, pp. 187-189 (1980).

Whiteside et al., "Development of a Methodology for the Production of Foot-and-Mouth Disease Virus" Develop. Bio. Standard, vol. 42, pp. 113-119 (1979).

APPARATUS FOR CULTURING ANIMAL CELLS

BACKGROUND OF THE INVENTION

The present invention relates to the propagation of animal cells for the purpose of recovering cell-secreted products of interest therefrom, and more particularly to an apparatus and process for the large-scale propagation of animal cells for such purpose.

It has long been known that animal cells, particularly human cells, secrete in vivo a wide variety of protein products which, directly or indirectly, are responsible for effecting particular functions or controlling or regulating particular functions in the species, including products such as hormones, enzymes, antibodies, clotting agents, and the like. It also has long been known that such naturally-secreted products, if capable of being isolated and recovered from an animal, offer enormous potential in the diagnostic and therapeutic fields.

Unfortunately, the amounts of these naturally-occurring products which are secreted by the cells of animals are generally very small, and isolation of such products per se, let alone in any useful quantity, is extraordinarily difficult and expensive.

It is generally accepted that a preferred route to production of useful quantities of natural cell-secreted products is by means of in vitro culture of the very animal cells which produce such products in vivo. While many natural product-secreting animal cells are not capable of sustained growth and subdivision in culture, there does exist a number of such cells (e.g., melanomas) which do possess this capability and which thus can be grown up in culture to cell densities at which useful quantities of their secreted products can be recovered. It is now also possible to "immortalize" animal cells which secrete a product of interest, but which otherwise are incapable of sustained growth and subdivision in culture, by, e.g., fusing them to a partner (e.g., a myeloma cell) which does possess such capability and which confers that capability to the hybrid cell, thereby enabling the in vitro culture of the hybrid cell line to produce significant quantities of the secreted product. Even in the realm of recombinant DNA technology, where heterologous genes coding for a particular product of interest are used to transform host cells, in vitro animal cell culture is of ever increasing importance due to the desire to employ animal cells as host cells in an effort to achieve recombinantly-produced products which are more like their naturally-secreted counterparts in terms of glycosylation and other structural/functional characteristics, and which are not at risk of being produced in association with undesirable products as could be the case utilizing bacteria as host cells.

The mere fact that a product-secreting cell, either naturally or by manipulation, possesses the inherent ability to undergo generally continuous growth and subdivision is, of course, insufficient by itself to enable its culture in vitro so as to produce and recover secreted product. The in vitro environment must be such as to provide the cells with the nutrition, oxygenation and other like requirements which induce and permit the cells to reproduce and secrete product.

Most successful in vitro animal cell culture devices and processes are of fairly small scale and are capable of producing only limited quantities of cell-secreted products. In many of these systems, the successful provision of a suitable environment for cell growth and product secretion is in part a consequence of the small scale, i.e., because the dimensions of the system are not very large, and also since the cell densities are often not extremely high, it is possible to provide an environment which is generally homogeneous in terms, e.g., of the concentration of nutrients and/or gases, and to which a large number of the cells can be exposed. Examples of such small-scale animal cell culture techniques and devices include roller bottles, stirred flask reactors, small hollow-fiber bioreactors and the like. In devices of this type, whether used for growth of anchorage-dependent cells or cells which can be grown in suspension, the rotation, stirring or short flow paths, often coupled with reasonably low cell densities, permits the establishment of a reasonably homogeneous environment capable of providing the requisite nutrition to most of the cells.

As more cell-secreted products of interest have become identified as of late, and as more uses for such products in diagnosis and therapy have been postulated and/or demonstrated, the demand is ever-increasing for production of such products in significant quantities. One obvious means for meeting this demand via in vitro animal cell culture is to make use of the heretofore proven small-scale methodologies and devices and simply increase the number of such units such that, in toto, many more cells are cultured and more secreted product produced. Among the difficulties in proceeding in this manner is that each such unit must be separately seeded, separately fed and gassed, separately observed and maintained, and separately processed to collect therefrom culture fluid containing secreted cell product, all of which adds enormously to the labor and equipment required and, hence, to the production cost (e.g., per gram) of the product of interest.

At least in theory, a far more economical route to large-scale production of secreted cell products via animal cell culture is simply to increase (i.e., scale-up) the capacity of a proven small-scale culture device such that it can accommodate many more cells and generate correspondingly larger quantities of product. Scale-up of these small-scale culture units has generally been quite unsuccessful, however, i.e., their capacity cannot be increased cost effectively while still maintaining the process and product-producing efficiencies demonstrated in the small-scale units. In large part, this inability is due to the difficulty of achieving any reasonable degree of homogeneity in the in vitro environment per se, and the further inability to expose even a majority of cells in high density clusters to the requisite nutrition and gas components of the culture medium.

Certain cell culture designs have demonstrated at least some degree of scaleability, such as air-lift reactors, stirred tank reactors and fluidized bed reactors. For large-scale culturing of anchorage-dependent cells, the stirred tank reactor and fluidized bed reactor can be employed by propagating the cells on or within solid carriers which, in turn, are maintained in suspension in the in vitro environment. However, these carrier systems are not presently capable of supporting the growth of all anchorage-dependent cell lines of interest and, in scaled-up systems, often-times exhibit reduced levels of product secretion as compared to that found in small, laboratory-scale units.

For growth of anchorage-dependent cells, glass bead packed bed reactors have been known for some time, and our own studies have demonstrated that such reactors, in small scale (i.e., from about 1 to 4 liter bead volume), are highly effective for use in continuous culture both of anchorage-dependent cells, where the cells attach to and grow on the bead surfaces, and of cells which do not require attachment for growth, where the cells are confined within and grow in the void spaces of the packed bed. Additional advantages of this reactor design are that it can be inoculated at relatively low cell densities (e.g., as low as 1/100 of the final cell density), thereby permitting use of a small number of seed vessels and related manipulations, while attaining and supporting high cell densities over long periods of time.

Unfortunately, despite indication in the art that glass bead packed bed culture units can be scaled up to industrial levels (an indication based upon results of short term batch propagation of particular cells to produce a particular virus), our studies have demonstrated that such reactors pose quite significant scale-up problems when long-term continuous culture is desired. As the glass bead bed height is increased to provide either greater surface area for attachment and growth, or greater void space for accommodation and growth, of the large number of anchorage-dependent or non-anchorage-dependent cells required for industrial-scale processing, medium to be perfused through the bed for nourishing the cells becomes increasingly less capable of achieving that result by reason of increasing depletion of the nutrients or gases therein over the length of the bed as they are consumed by the cells. As a consequence, significant cell density gradients exist throughout the length of the bed. In addition, uneven distribution of cells or cellular material throughout the bed brings about channelling and by-passing of medium through the bed (i.e., the seeking out of preferential flow paths offering least resistance), leading to non-uniform growth conditions.

In short, glass bead packed bed reactor units can easily be scaled-up in size per se (i.e., made larger), but only at a significant loss of process and product-production efficiency and at a significant loss in the ability to easily translate to large scale, if at all, the nutrition and other growth and product-secretion parameters determined to be optimum for a particular cell line in small-scale laboratory tests. Without this latter ability, each scale-up ends up requiring a comprehensive development program to reestablish operable and/or optimum growth conditions, nutrient requirements and the like, adding enormously to the costs of production when just the opposite is desired.

SUMMARY OF THE INVENTION

The primary object of the present invention is to provide an in vitro cell culture system for animal cells, based upon the principles of glass bead packed bed culture systems, which can be readily, economically and predictably scaled-up to accommodate and effect large-scale production of secreted cell products of interest.

According to the invention, a culture system is provided based upon a vertically stacked arrangement, within a common housing, of two or more culture subunits each containing a packed bed of carrier particles (e.g., glass beads) upon which growth of anchorage-dependent animal cells can occur or in the void space of which growth of non-anchorage-dependent animal cells can occur. A single feed of culture medium is provided to the housed arrangement and therein serves as a separate feed of culture medium to each culture subunit. In addition, spent culture fluid, having passed through the packed bed and thus having its nutrients depleted by the growing cells affixed to or entrapped between the bed particles and having collected from the cells secreted cell products, including secreted cell proteins of interest, exits from each separate culture subunit and is communicated to a common spent culture fluid conduit where it commingles with spent culture fluid from all other culture subunits within the housing for removal from the housed arrangement and further processing to recover secreted cell proteins of interest.

By virtue of the culture system of the present invention, each culture subunit is sized so as to present a depth of carrier particle bed which is substantially the same as that commonly employed in conducting preliminary experiments on growth conditions, flow characteristics, nutrient and gassing requirements, product secretion characteristics and rates, and other like parameters, for particular cell lines. For scale-up to larger scale production, the culture subunits are simply multiplied in number and arranged within the common housing provided by the invention and/or increased in volume, without substantial change in the depth of the packed bed. Since each culture subunit operates as an independent culture device, the majority of operating characteristics (particularly flow characteristics) and operating results established for a particular cell line and a particular bed of carrier particles are directly, and predictably, applicable to the scaled-up system. At the same time, however, the culture medium feed and product (spent culture fluid) collection system is arranged to be common for all culture subunits so that, in terms of medium processing, gassing, product collection, maintenance, sampling and the like, the multi-subunit reactor system essentially operates as a single culture unit in gross.

As will be readily apparent from the more detailed description which follows, the culture system of the present invention enables both scale-up and scale-down of a culture operation in a predictable and economic manner, generally involving simply the addition or subtraction of discrete culture subunits within the housed system and/or increase or decrease in the volume of each culture subunit while generally maintaining a packed bed height substantially the same as that employed in a culture system (be it a single or multi-subunit one) of smaller or larger capacity for which operating parameters and characteristics have already been established.

As described in further detail hereinafter, the essential feature of the invention is a housed multi-subunit culture system, with each subunit being a separate culture chamber unto itself. Generally, each subunit can be described as a basket-like enclosure or receptacle which is either a separable enclosure per se or is formed at least in part by portions of the housing. Each basket-like enclosure (culture subunit) has a base and a surrounding, upstanding side wall and, positioned above the plane of the base a perforate or porous plate upon which the packed bed of carrier particles resides, and through which spent culture fluid, having passed through the bed, can flow into a liquid collection space defined by the area between the base and the perforate plate. The collection space of each culture subunit is in liquid communication with a common conduit, generally defined by a hollow stem in association with one or more of the subunits, such that spent culture fluid from each unit is commingled for egress from the housed arrangement and further processing.

DETAILED DESCRIPTION OF THE INVENTION

Figure 1:
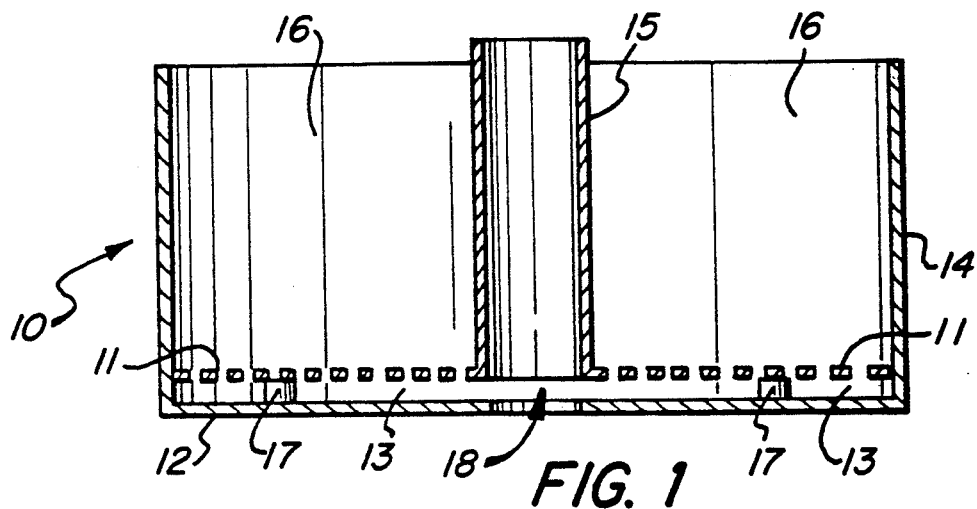
FIG. 1 is a cross-sectional view of a single cylindrical culture subunit which can be added to a housed culture arrangement for scale-up thereof.

In the detailed description which follows, having reference to the figures, there is first described a single basket-like culture subunit which can form the basis for multi-stage scale-up of the culture system and/or for scale-up by increase of subunit volume without substantial increase in carrier particle bed depth. As will be apparent from the further description, this first integral subunit so described need not necessarily be present as such (i.e., as an integral unit in the form shown) in order to provide a highly useful, scaleable system according to the invention (see, e.g., FIG. 9), although it is employed in preferred embodiments of the invention containing three or more subunits (see, e.g., FIGS. 7 and 8). It is, however, first presented as a means for illustrating various details not only of this subunit but also of subunits which may differ in other details.

For the purpose of the detailed description, the culture system is described with reference to cylindrical basket-like subunits and a common cylindrical housing therefor, since such geometry is the preferred means for accommodating maximized culture volume and ease of construction. As will be apparent, however, other geometric configurations, while perhaps less desirable, also may be employed.

In accordance with specific aspects of the invention, and with reference to the accompanying figures, there is provided as a fundamental component of the culture system a basket-like element or receptacle 10 (shown in cross-section in FIG. 1) adapted to receive and retain a plurality of carrier particles (generally glass beads) upon which growth of anchorage-dependent animal cells can occur or between the voids of which growth of non-anchorage-dependent animal cells can occur. The cylindrical basket element is comprised of a base section 12 and upstanding surrounding side wall 14 extending from the periphery of the base section which serves to define an enclosed space 16 for receiving glass beads. The base section 12 and side wall 14 are made of solid and liquid impervious material compatible with animal cell culture, such as plastic or stainless steel, and are either integral surfaces or affixed in a way so as to provide a liquid-tight enclosure.

Arranged in circular base section 12, generally at the center thereof, is a liquid outlet opening 18 through which spent culture fluid may flow out of the basket enclosure. The basket element further contains a generally rigid perforate or porous plate element 11, generally in the nature of a screen or rigid mesh, of substantially the same planar area and configuration of base section 12 (i.e., extending out to side wall 14 so as to be very close thereto or, preferably, in contact therewith) and disposed a small distance above base section 12 so as to define a culture fluid collection space 13 therebetween which is in fluid communication with outlet 18 in base section 12. The degree of and size of perforation or porosity of perforate base plate 11 is chosen so as to prevent passage therethrough of glass beads which rest on and lie above it, while permitting spent culture fluid to pass through it to collection space 13.

Basket element 10 further comprises a hollow stem 15 made of solid and liquid-impervious material which extends from a position over outlet 18 and vertically into the basket interior. Stem 15 is open at its terminal portions so as to enable it to serve as a conduit through which spent culture fluid may flow, e.g., as part of a conduit system for receiving spent culture fluid from the collection spaces of other culture subunits arranged within the common housing.

In the preferred form of construction of basket element 10, the portion comprised of base section 12 and side wall enclosure 14 is provided as a single receptacle element, having liquid outlet 18 arranged in base section 12. A second insert element is provided comprised of hollow stem 15 (open at its terminal portions) and, affixed thereto at or near its lower end, porous base element 11 (see FIG. 2). The underside of porous base element 11 (or alternatively, the upper side of base section 12) is provided with stand-off or spacer elements (e.g., elements 17 in FIG. 1) such that, when the portion shown in FIG. 2 is inserted into the enclosure formed by base section 12 and side wall 14, the porous base element 11 occupies horizontal plane which is a small predetermined distance above the plane of base section 12, thereby defining a collection space 13. This same effect can be accomplished with a number of fingers emanating from about the inner periphery of side wall 14 and upon which the stem/porous plate element can be rested and supported a small predetermined distance above the plane of base section 12.

Figure 3:
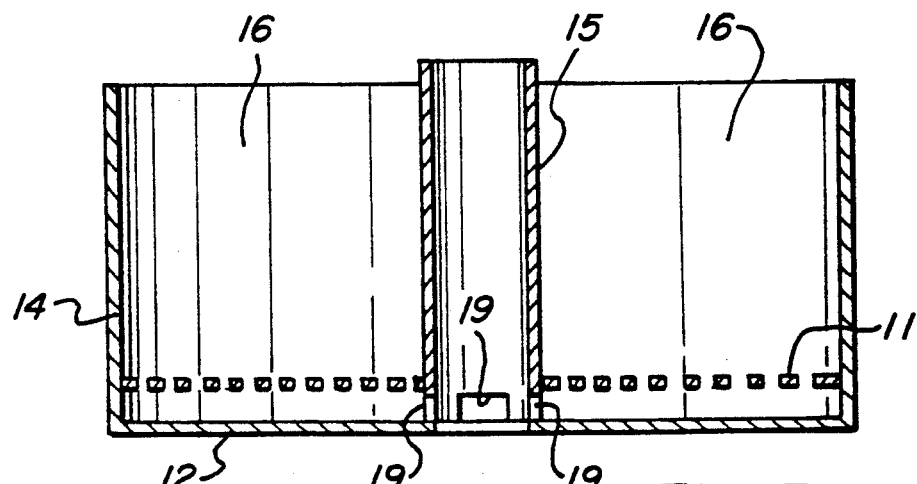
FIGS. 3 and 4 are cross-sectional views of basket-like culture subunits such as shown in FIG. 1 illustrating different arrangements of the stem element.
Figure 4:
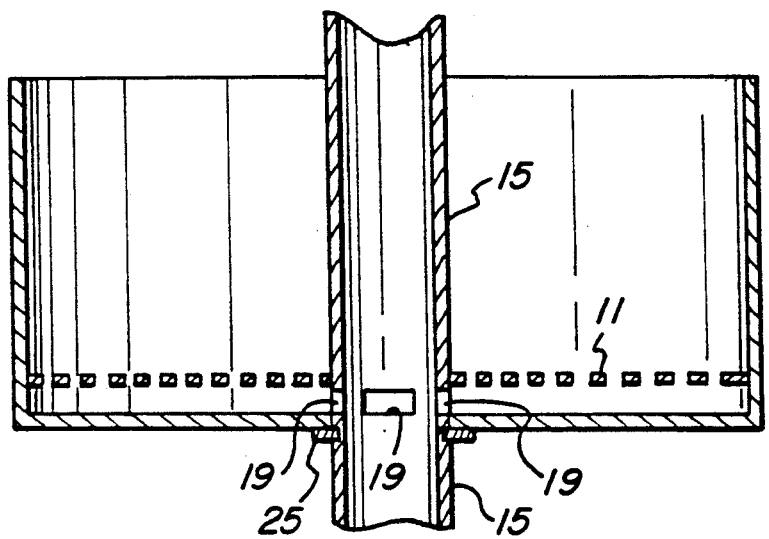

In an alternative embodiment, it is possible to arrange stem 15 to be integral with base section 12, i.e., a bottom portion of stem 15 can be affixed at or within liquid outlet opening 18 of base section 12, as shown in FIGS. 3 and 4. In constructions of this type, stem 15, in the area which lies within collection space 13, is provided about its periphery with a number of discontinuous fluid openings 19 so as to enable spent culture fluid in collection space 13 to enter the hollow interior of stem 15. Also in such cases, porous base element 11 can be either permanently affixed, a short predetermined distance above base section 12, along the inner periphery of side wall 14, or alternatively, can simply be adapted to fit over stem 15 and, by virtue of stand-offs on the porous base element or base section 12, or protruding fingers from side wall 14, be arranged to reside a small distance above base section 12 for purposes of defining collection space 13.

Figure 5:
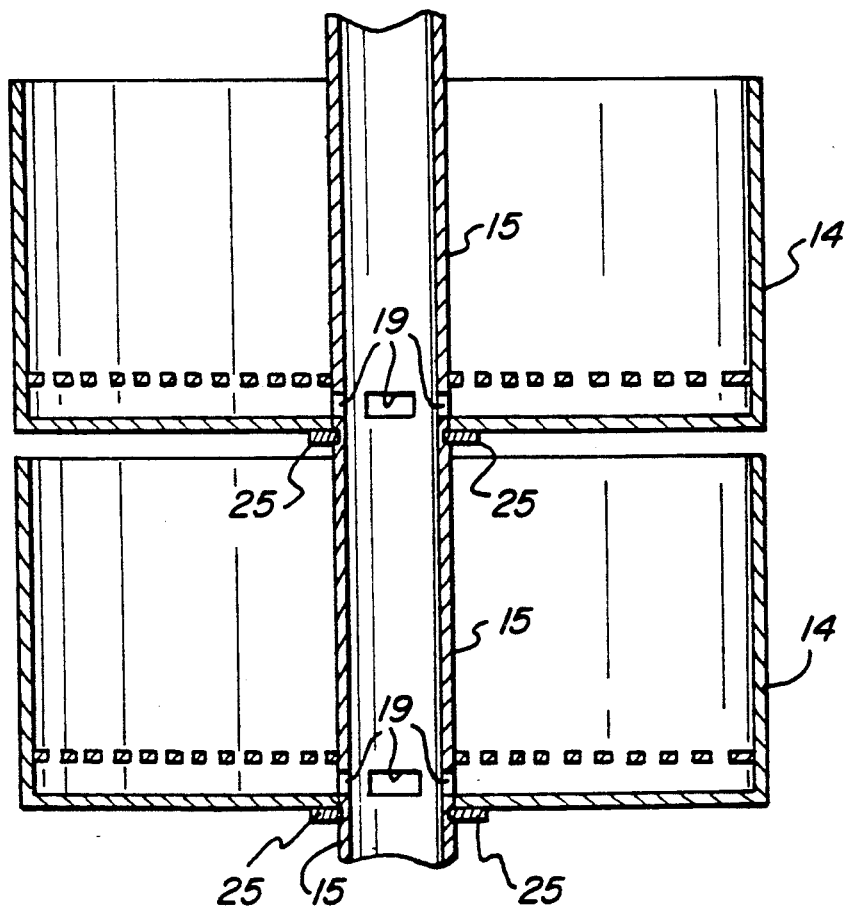
FIG. 5 is a cross-sectional view of two culture subunit enclosures arranged along a common stem.

In yet another embodiment, as shown in FIG. 5, stem 15 can be in the form of an elongate stem, not affixed to either base section 12 or porous base element 11 but supported elsewhere, along which are provided a number of discontinuous stops or a continuous collar (e.g., collar 25) upon which the base section 12 of a basket can rest so as to support the basket at a predetermined location on the stem. Here again, the stem 15, in the area or areas which will lie within a collection space or spaces, will be provided about its periphery with a number of discontinuous fluid openings 19 to permit spent culture fluid in the collection space 13 to enter the hollow interior of the stem.

Figure 6:
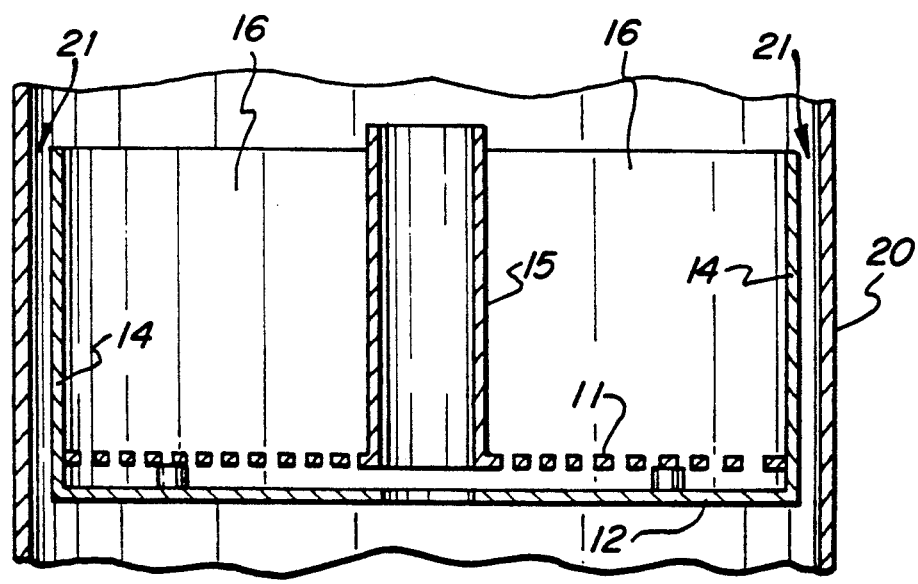
FIG. 6 is a cross-sectional view of a single basket-like subunit such as shown in FIG. 1 within a housing.

For use in the culture of animal cells, basket subunit 10 is arranged within a housing 20 (see FIG. 6) which is of the same general geometric shape as the basket subunit, e.g., a cylindrical housing for cylindrical basket elements. The cross-sectional dimensions of the housing 20 are such that, when basket subunit 10 is arranged therein, a small predetermined annular culture medium feed space 21 exists between the inner peripheral surface of the housing 20 and the outer peripheral surface of the basket subunit 10. The housing 20 is made of solid and fluid impervious material, such as plastic (e.g., polycarbonate) or stainless steel.

For arranging a basket subunit to occupy a fixed vertical position within housing 20, use can be made, for example, of stops or a collar along a unitary elongated stem 15, as shown in FIG. 5, or, in the preferred embodiment as described hereinafter, by stacking upon stems of predetermined heights.

Figure 7:
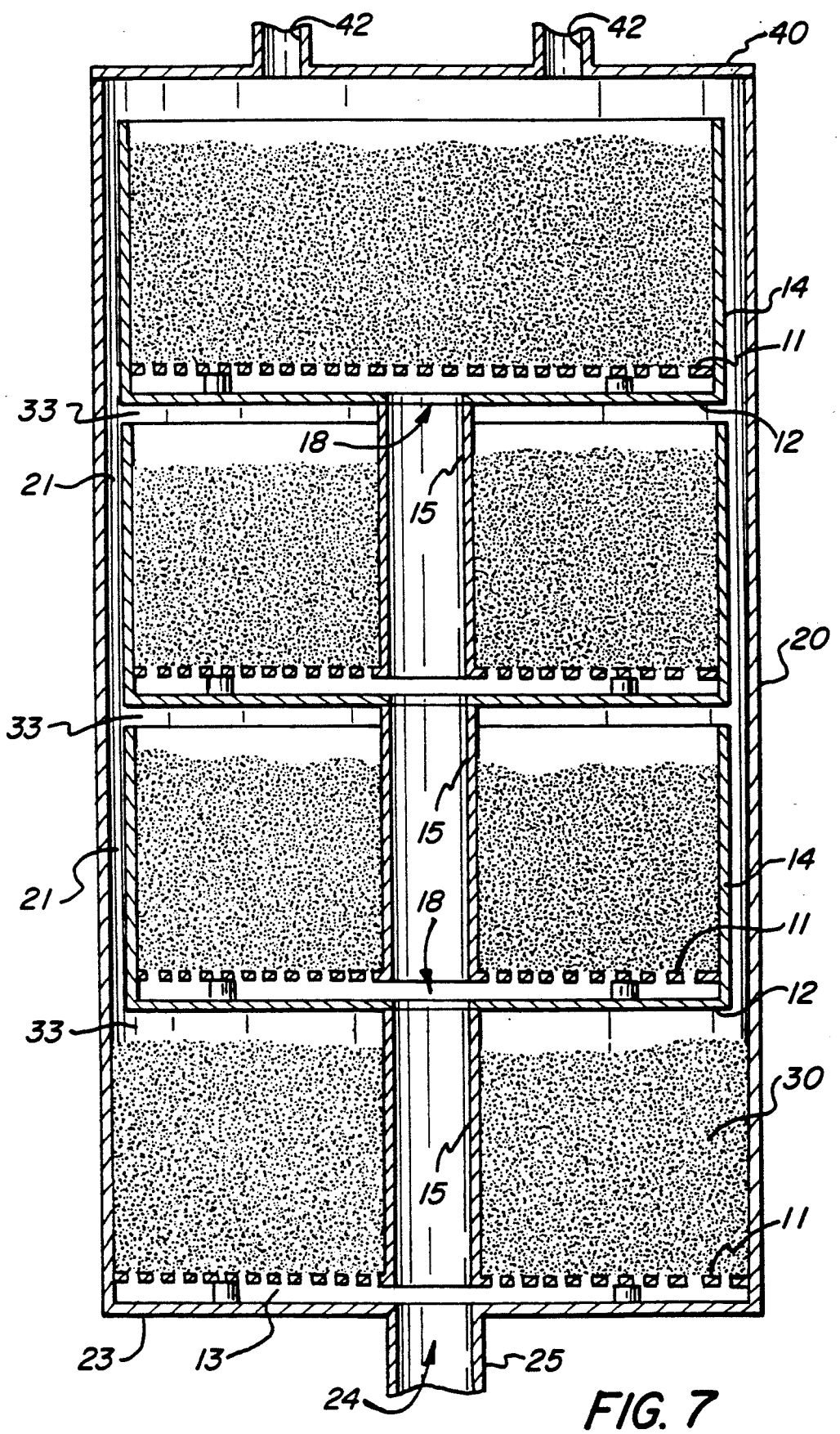
FIG. 7 is a cross-sectional view of a multi-stage culture system according to the invention consisting of four culture subunits within a common housing.

FIG. 7 illustrates a culture system according to a preferred embodiment of the invention. In this system, cylindrical housing 20 is provided, in its circular base section 23, with liquid outlet opening 24 which in turn can be affixed to a liquid outlet tube 25. For assembling the culture system, there is first provided in the lower portion of the housing an element such as shown in FIG. 2 comprised of a perforate or porous circular plate 11 having a centrally-disposed circular opening and, affixed to the plate at the circular opening, an upstanding hollow stem 15 which is of a predetermined height. By virtue of stand-off elements emanating from either the underside of the porous plate or the upper side of base section 23, or finger supports protruding from the side wall of the housing, the porous plate 11 is disposed in a horizontal plane above that of the base section 23 so as to define therebetween a collection space 13 which is in liquid communication with liquid outlet opening 24. In the bottom section of the housing, this porous plate 11 is sized so as to be of nearly the same diameter as that of the housing so as to prevent glass beads 30 from entering the collection space 13 and, as previously noted, is of a porosity so as to be liquid permeable but at the same time prevent glass beads lying on and above it to pass through to the collection space. In this manner, a basket-like culture subunit is formed in this lower section of housing 20 from the side walls of the housing itself, the base section 23 of the housing, the porous plate 11 lying above base section 23, and the upstanding stem 15.

This basket-like culture subunit in the bottom of housing 20 is packed with glass beads 30 to a uniform height therein such that a predetermined portion of hollow stem 15 extends above the packing.

Figure 2:
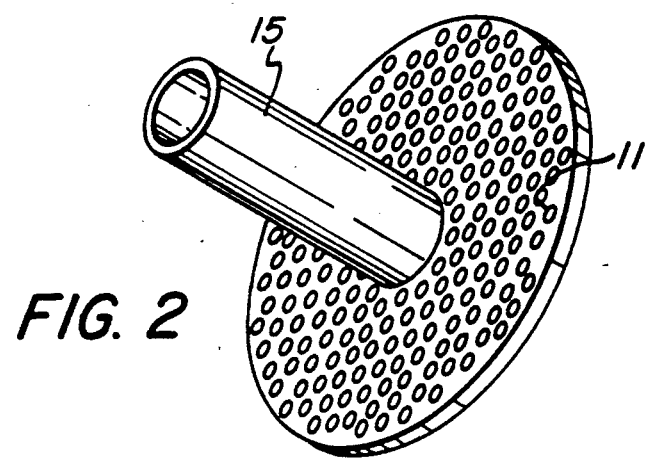
FIG. 2 is a perspective view of a combined stem and perforate plate element utilized in forming a culture subunit according to the invention.

In continuing the construction of the culture system, there is next arranged within the housing 20 a basket enclosure element such as shown in FIG. 1 defined by base section 12, having a centrally-disposed circular opening 18, and surrounding side wall 14 upstanding from the periphery of base section 12. As earlier noted, the cross-sectional diameter of this basket enclosure element is smaller than that of the housing 20 so that an annular culture medium feed space 21 exists between the inner peripheral surface of housing 20 and the outer peripheral surface of surrounding side wall 14. The basket enclosure element, at its base section 12, is caused to rest upon and is supported by the hollow stem 15 previously-arranged in the bottom section of the housing, so that the circular opening 18 in base section 12 is coincident with the upper circular opening of hollow stem 15. For increasing support of the basket enclosure element and for improving the liquid seal between the hollow stem and the opening 18, the upper circular opening of stem 15 preferably should be flanged as shown in FIG. 7. By reason of the predetermined height of the stem 15, the base section 12 of the basket enclosure supported by stem 15 is horizontally disposed a small predetermined distance above the plane of the packed glass beads in the culture section below so as to define a space 33 into which culture medium, passing down the annular space 21, can gain access to the glass bead bed.

The basket enclosure is then fitted with an element as shown in FIG. 2 comprised of a porous plate 11 and stem 15, all as described previously with respect to the lower section of housing 20, with the exception that the porous plate 11 is sized to fit within surrounding side wall 14 rather than the housing side wall.

As in the lower section, glass beads are packed into this basket-like culture subunit to a predetermined height such that a portion of stem 15 extends above the glass bead bed.

In continuing the arrangement of the culture system, another basket-like culture subunit identical to that just described is arranged above the previously-arranged subunit, being supported by the stem 15 of that previously-arranged section.

In completing the construction of the culture system, a final basket enclosure is arranged above the previous one. This final basket enclosure is comprised of a base section 12 (having a centrally-disposed circular opening 18 therein) and surrounding side wall 14, and is supported by the stem 15 of the previous culture subunit. In contrast to the earlier culture subunits, this final subunit need not have a stem and, thus, it is necessary only to arrange above the base section 12 a porous base plate 11 on which the glass beads will rest. Also, owing to its porosity, it is not necessary for this base plate 11 in this final section to have a defined circular opening therein in order to permit liquid communication with liquid outlet opening 18.

Lastly, a top section 40 is used to close the housing, and is provided with one or more openings 42 through which fresh culture medium can be supplied to the culture system. This closure portion can also be provided with distributor elements or plates so as to enable uniform distribution of fresh culture medium from one or more feed entry points.

Figure 8:
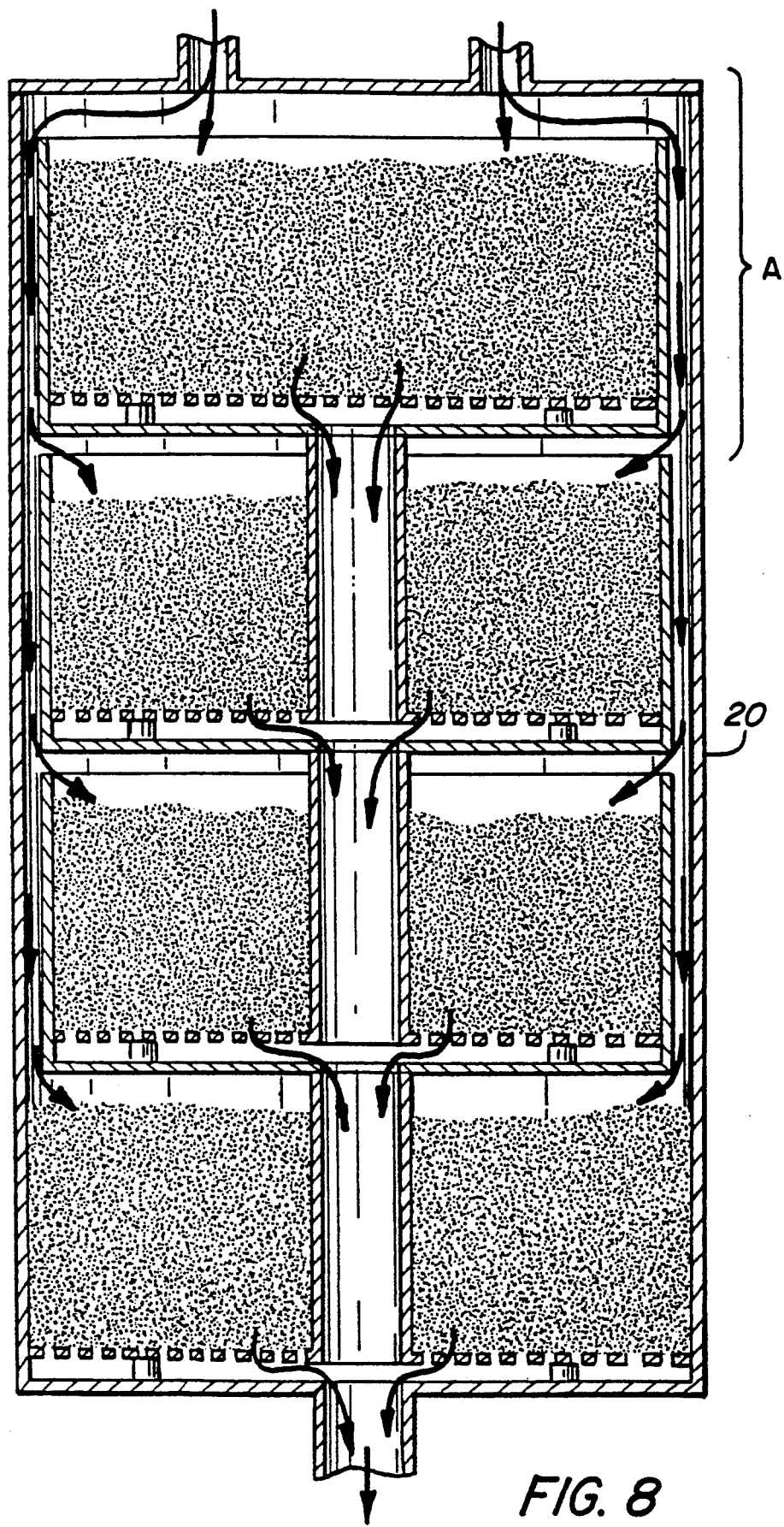
FIG. 8 is a cross-sectional view of the apparatus shown in FIG. 7 which illustrates the flow of culture medium and spent culture fluid throughout the system.

As shown schematically in FIG. 8, operation of the culture system of FIG. 7 is such that fresh culture medium is supplied through the top section of the housing and caused to flow directly into the glass bead bed (containing an inoculum of cells) in the first upper section (designated A) and also to flow into and down the annular culture feed space between the housing side wall and the basket subunit side walls. This down-flowing fresh culture medium, as shown by the arrows, feeds each of the remaining culture subunits in parallel.

Culture medium fed in this way to each subunit bed of glass beads percolates through the bed to nourish the cells growing in contact with the glass beads, all the while being depleted of its nutrients and gases while collecting protein of interest and other cell-secreted products. When it reaches the bottom of the bed of glass beads, the spent culture medium passes through the porous base plate supporting the bed and into the collection space under the bed. From this point, the spent culture medium flows into and out of the liquid outlet opening in the bottom of the culture subunit and thus into the common spent culture medium collection conduit formed by the interiors of the various hollow stems 15 associated with the individual culture subunits. The commingled flows of spent culture medium exit from the housed arrangement through the bottom of the housing.

In the embodiment illustrated in FIGS. 7 and 8, the flow of fresh medium is shown as being from top to bottom as is the flow of spent culture medium through the various stems 15. As will be apparent, however, it can be arranged through suitable pumping mechanisms for the spent culture medium to flow upward through the stems, i.e., counter-current to the flow of fresh medium, for exit from the culture system through the same top portion where fresh medium is fed, in which case there is no need for the liquid outlet opening 24 or liquid outlet tube 25 at the bottom of the housing, provision instead being made for a stem in the uppermost culture subunit and a liquid outlet opening in communication therewith at the top of the housing. In yet another alternative mode of operation, the fresh culture medium can be fed upward through the culture system, and spent culture medium, having passed downwardly through a bed of glass beads, then flowed upward or downward through the system for exit at an appropriate outlet opening in the housing.

The vertical housed assembly of culture subunits, having a common feed source and common spent medium collection path yet otherwise operating as separate, independent culture units, possesses as its primary advantage the means for being scaled up or down depending upon production requirements simply by addition or subtraction of one or more of the culture subunits, all the while maintaining commonality in feed streams and collection streams, along with appropriate adjustment, if necessary, of culture medium flow rates, etc. to take into account increasing or decreasing length of travel through the housed assembly. Since the culture subunits act as individual culture chambers in parallel, characteristics of flow throughout the bed, gassing requirements, nutrients needed to support particular cell density, and other like parameters, are essentially unchanged from those established for the basic subunit per se, whether the subunit is used along with one, two, three or more additional subunits, thus enabling direct and predictable scale-up from laboratory scale conditions.

As previously noted, and as further described hereinafter, scale-up also can be readily and predictably accomplished by increasing the volume of each culture subunit while maintaining approximately the same depth of packing material in each subunit, i.e., by simply increasing the radius of the subunits and, of course, the housing in which the subunits are arranged.

Figure 9:
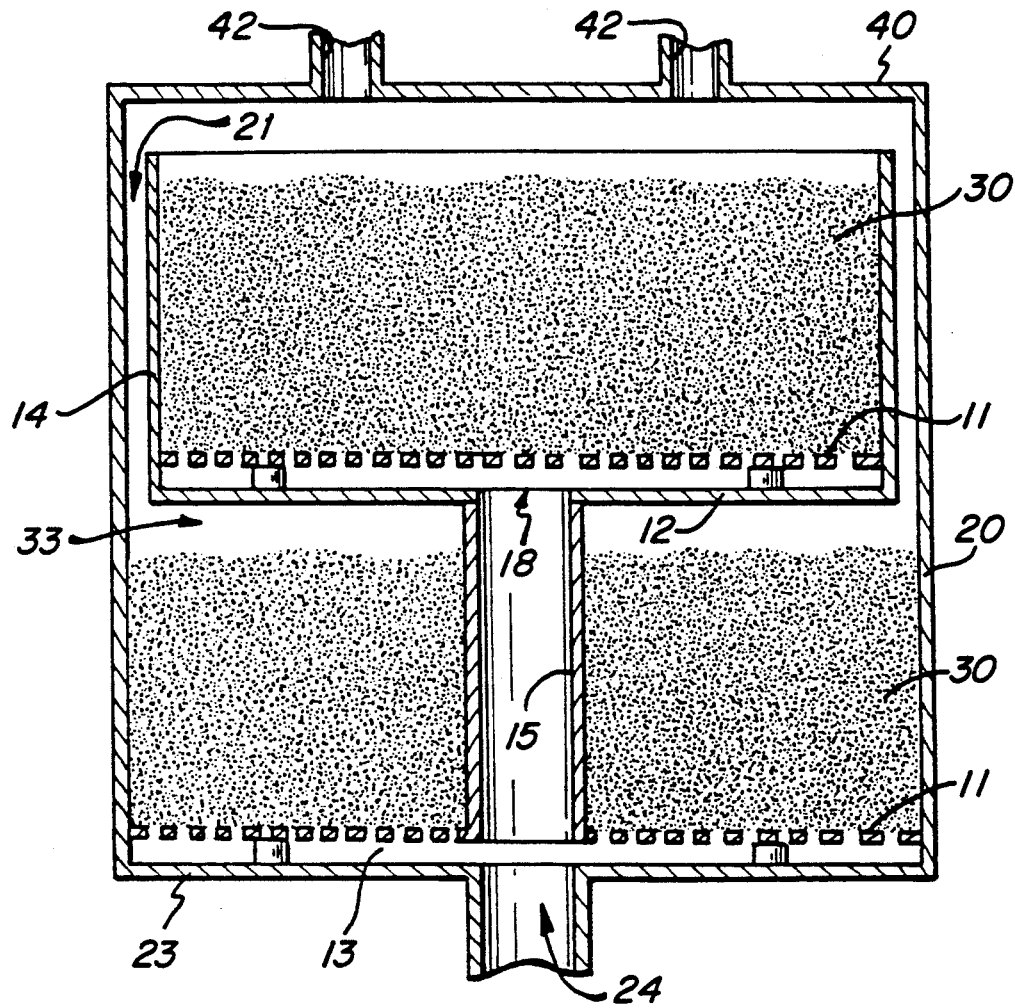
FIG. 9 is a cross-sectional view of a two-stage culture system according to the invention.

In the simplest form of a multi-subunit culture system, e.g., for a downward flow of fresh medium and downward collection of spent medium, the culture system consists of two separate subunits as shown in FIG. 9. In this arrangement, the first culture subunit is an enclosure formed by the walls of housing 20 and its base section 23 (arranged with an exit port 24), having a perforate base plate 11 extending out to the housing side wall, and also having an exit port or opening therein overlying the exit port 24, the base plate 11 being positioned above base section 23 to provide collection space 13. Emanating from the opening in the base plate is stem 15 which rises into the enclosure and terminates, at its hollow upper end, a short distance above the plane of the glass bead packing therein. Located above this first subunit is a second subunit, this time comprised of a basket enclosure discrete from the housing, having a base section 12 (with a liquid outlet port 18 lying above the open upper end of hollow stem 15) and surrounding side wall 14, the basket enclosure occupying a fixed vertical position above the first subunit, e.g., by resting upon stem 15. The second subunit has its own perforate base plate 11 above which the glass bead bed is arranged, and the entire subunit is sized such that a culture feed space 21 exists between the housing wall and the side wall 14 of the subunit. In addition, the fixed vertical position of the second upper subunit is such as to leave a culture feed space 33 between the bottom of base section 12 and the top of the glass bead bed in the first subunit, as can be easily accomplished by making stem 15 a height that extends above the height of the bed packing in the bottom subunit. Culture medium fed to the housed system from its top directly feeds the glass bead bed in the second (upper) subunit and feeds the glass bead bed in the first (lower) subunit by passing through feed space 21 and into feed space 33 above the glass bead bed. Spent medium from the second (upper) subunit passes through perforate plate 11 into collection space 13, into and out of outlet port 18 and into the hollow interior of stem 15. Spent medium from the first (lower) subunit passes through its perforate plate 11, into its collection space 13, and into outlet opening 24 where it commingles with spent medium from the upper unit, flowing in stem 15, for exit through the bottom of the housing.

For scaling-up the system shown in FIG. 9, there may be added to the system one or more self-contained basket-like subunits such as shown in FIG. 1, configured to maintain feed space 21 throughout the housed system, and each having a perforate base plate 11 and stem 15 for stacking one unit above another and for carrying out the common spent medium collection flow through the interiors of all the stems.

The system of the present invention also enables scale-up by maintaining the same number of subunits but increasing the volume of each by increasing the cross-section of each with little or no change in bed height. In this manner, the various bed flow characteristics established on a laboratory basis for particular bed heights are essentially the same and can be directly translated to the beds of increased volume, with changes where appropriate in culture medium flow rates to accommodate the increased capacity of each subunit. Also, of course, a combination of these scale-up techniques can be employed.

Figure 10:
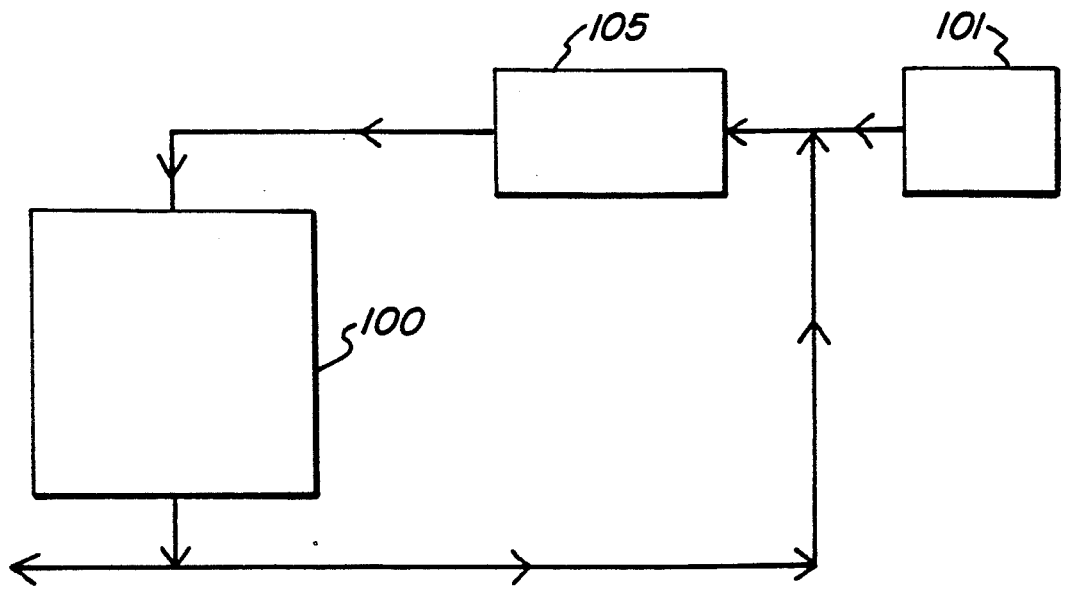
FIG. 10 is a schematic of a culture process employing the housed culture system of the invention.

The culture system of the present invention forms the fundamental portion of an overall animal cell culture process which can take a variety of forms in terms of medium flow, gassing and the like. A typical such process is illustrated in FIG. 10 where the overall culture unit is designated as 100. Fresh medium 101 at appropriate temperature for culture of living animal cells (e.g., 37° C.) is passed through a suitable lung arrangement 105 to provide the medium with $O_2$ and $CO_2$ necessary to support cell growth, maintain pH, etc. and is then pumped to the top of the housed culture assembly 100. Spent culture medium removed from the bottom of the culture assembly is then divided into a portion for processing to recover secreted cell proteins and a portion for recirculation, with fresh medium supplementation, through the lung and through the culture assembly. Sample ports can be arranged throughout the recirculation loop to monitor nutrients, gases, pH, and the like.

The housed culture assembly is generally employed in a continuous culture system to maximize production of secreted cell proteins per unit time.

To illustrate the scaleability of the culture system of the present invention, a culture system essentially as shown in FIG. 9 (i.e., a bottom cylindrical subunit defined by the cylindrical housing bottom and housing walls, and an upper cylindrical subunit defined by a discrete basket-like enclosure arranged within the housing) was employed having a total volume of glass beads packed into the two subunits of 12 liters. The subunits were separately inoculated with a continuous cell line known to produce and secrete a protein of interest which can easily be assayed to determine production rates of that protein on a per diem basis. The housed subunits were perfused with a defined culture medium warmed to 37° C. and which was provided with $O_2$ and $CO_2$ as required for the growth and maintenance of the cell line and for pH maintenance. The spent culture fluid collection stem in the bottom subunit was a one-inch diameter hollow stainless steel tube, affixed to a porous base plate (1/16-inch holes), and extending 5.125 inches vertically above the base plate, and having a collar about its upper periphery for supporting the upper basket. Six (6) stand-offs of 0.125 inches in height were arranged on the underside of the porous plate to produce a 0.125 inch high collection space between the porous plate and the bottom of the housing. The upper subunit basket was also provided with a one-inch hollow stainless steel stem affixed to a porous plate and extending 8.75 inches thereabove, so that a portion of the stem protruded through an opening in the top of the housing. As with the lower subunit, stand-offs were used to define a collection space 0.125 inches in height. The upper cylindrical basket was sized so that a uniform annular space 0.125 inches wide existed between the side walls of the housing and the side walls of the basket subunit. The packing of glass beads in the lower subunit was such that a space about 0.25 inches in height existed between the top of the packing and the base of the upper basket subunit. Medium was flowed to the top of the housing and spent culture fluid was removed from the top of the housing via the common interiors of the stems of each subunit.

Figure 11:
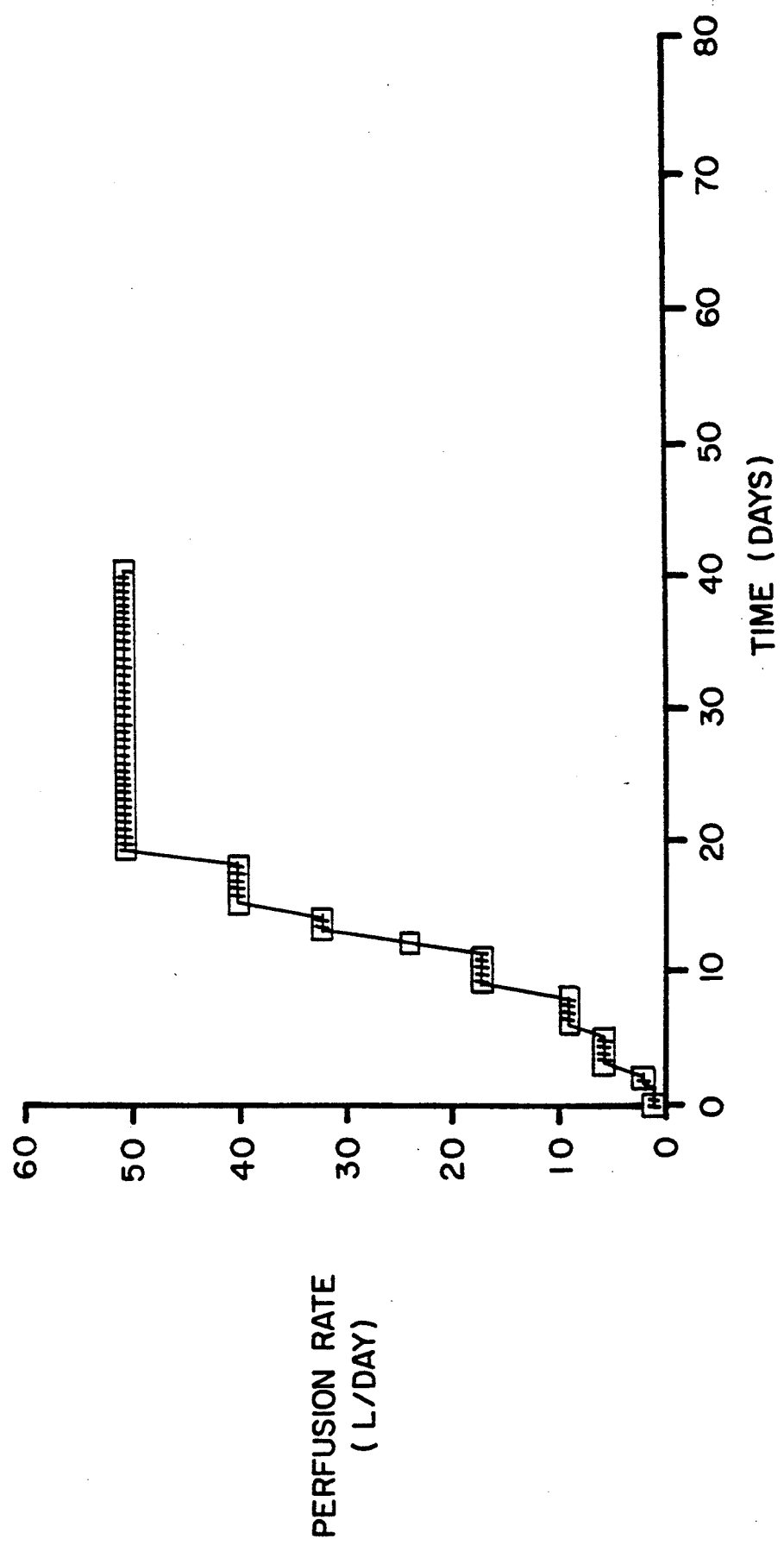
FIGS. 11, 12, 13 and 14 are graphical depictions of the results of scale-up experiments using the reactor system of the invention.
Figure 12:
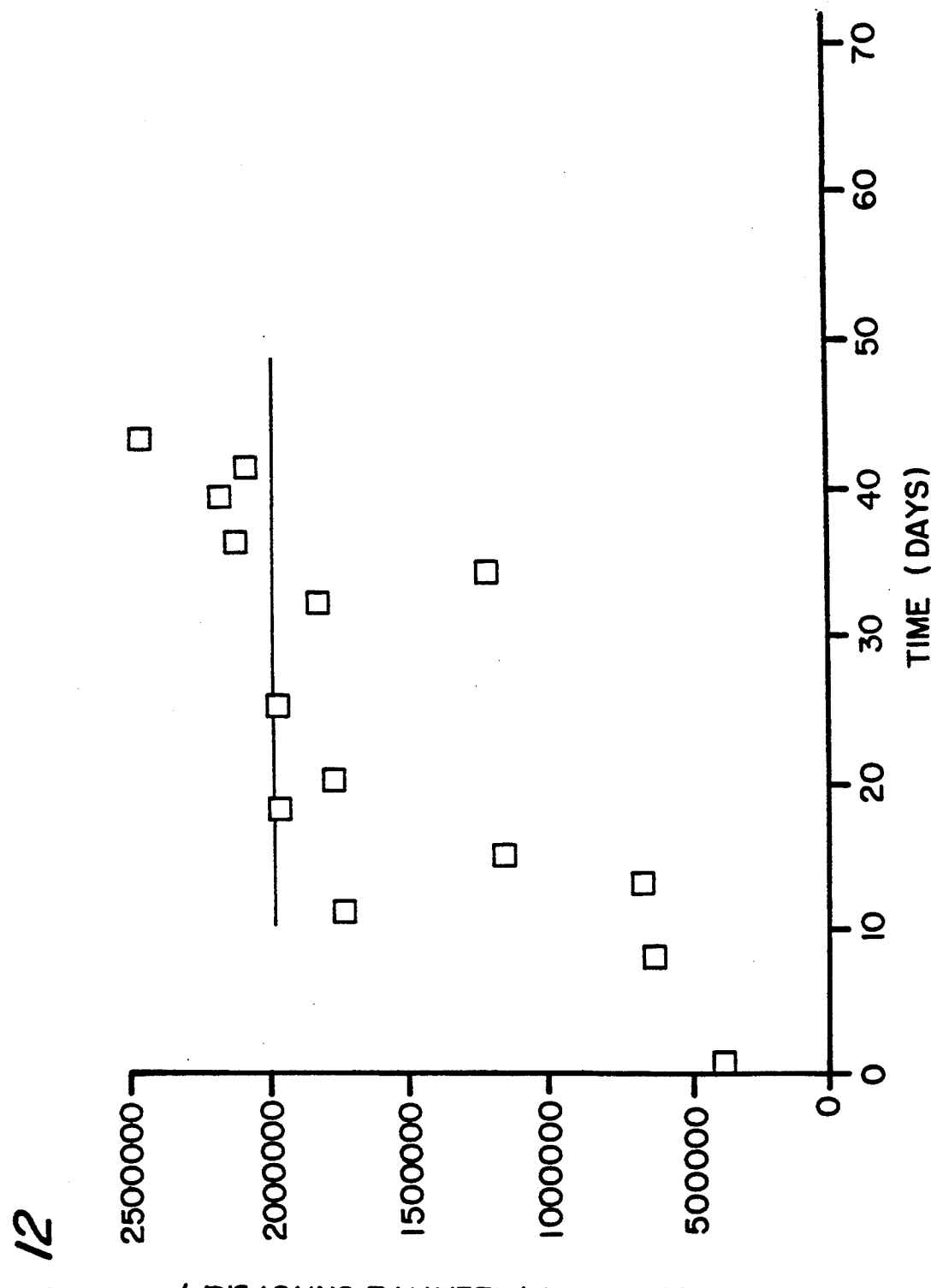

As shown in FIG. 11 the perfusion rate of medium (liters/day) was gradually increased as the cells grew to generally uniform steady-state cell density and then maintained at a constant rate of about 50 liters/day (in all cases, being a continuous culture system, spent culture fluid was drawn off at the same rate as culture medium being fed). At this constant rate of perfusion, the rate of production of the protein of interest (expressed as relative units/day, as shown in FIG. 12) averaged about $2 \times 10^6$ units/day.

Figure 13:
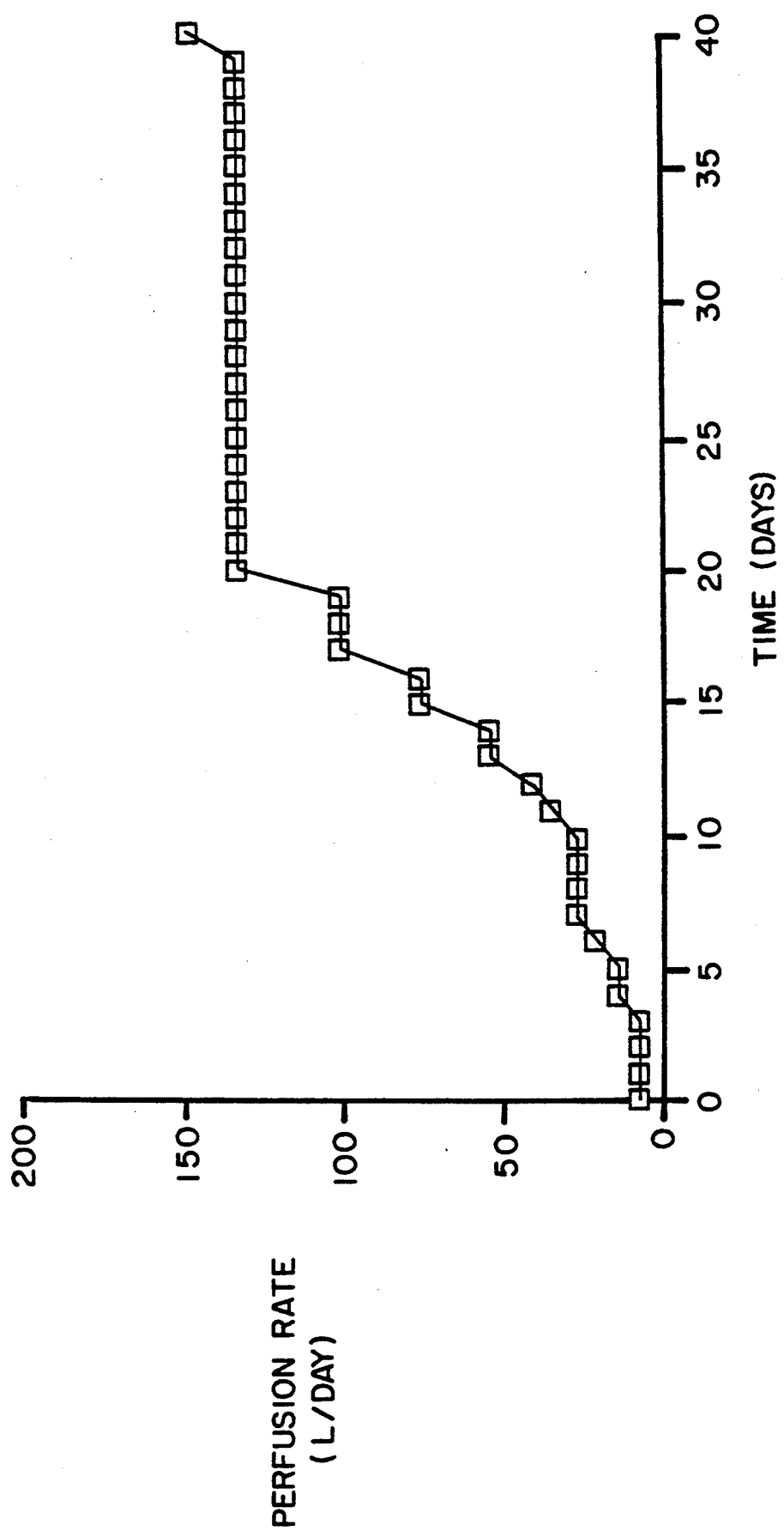
Figure 14:
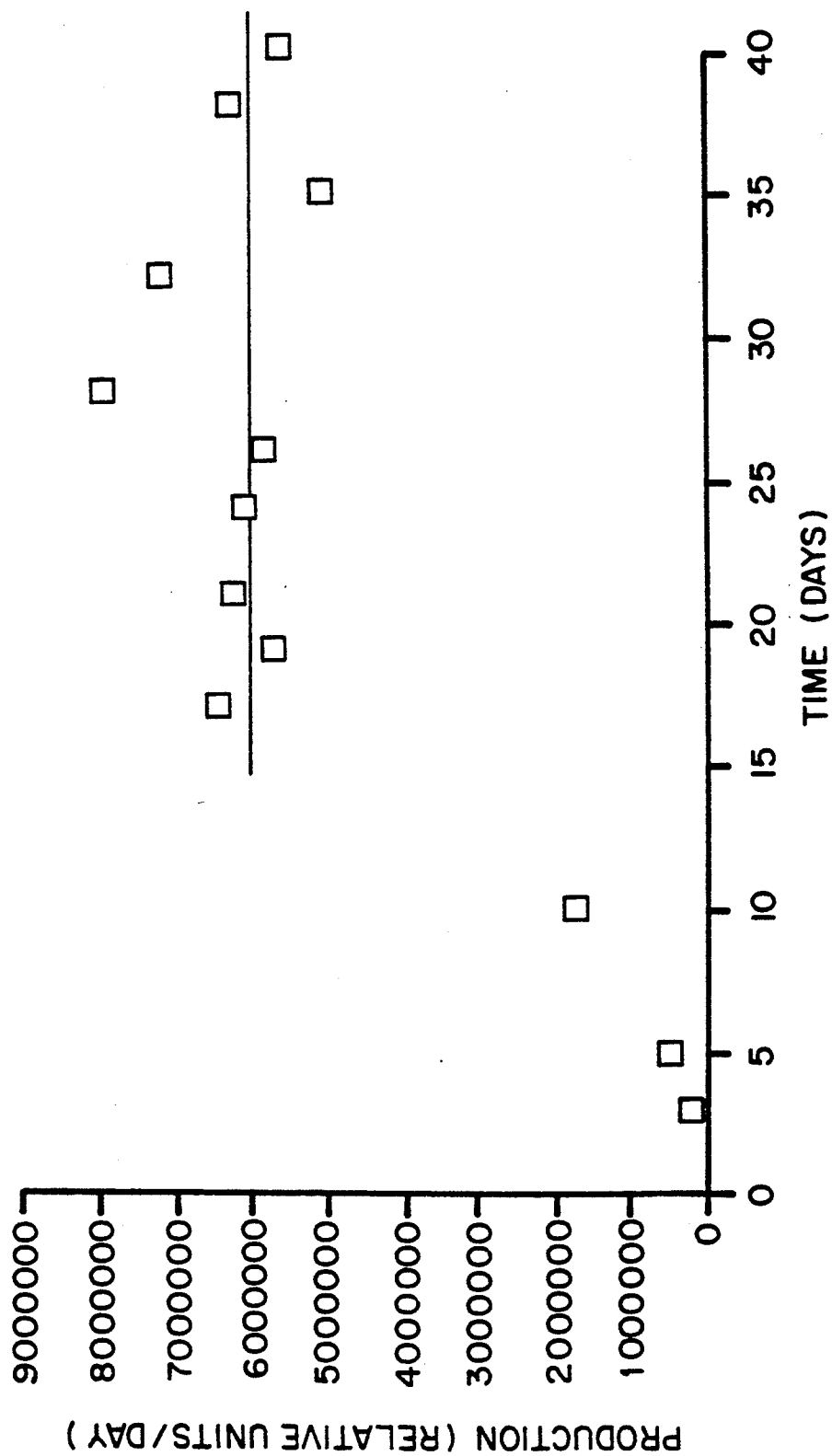

In a subsequent experiment, the same reactor configuration was maintained, but the volume of glass beads in the reactor was tripled, to 36 liters, by appropriately increasing the diameter of each of the subunits (and of the housing) without substantially changing the bed height in each subunit. Using the same cell line, medium and conditions, but with essentially a three-fold increase in perfusion rate (see FIG. 13), the per diem production rate of the housed culture system increased to an average of $6 \times 10^6$ units/day (see FIG. 14), indicating a near quantitative scale-up from the tripled-capacity unit.

As previously noted, the apparatus and process of the present invention is equally well-suited to the in vitro culture of anchorage-dependent animal cells and to the in vitro culture of animal cells which do not require attachment to surfaces in order to remain viable. In the former case, particular carrier particle bed parameters established for small-scale culture of a particular cell line are readily scaled-up to accommodate a larger number of cells either by increasing the number of subunits per se (each with the same carrier particle volume and bed height utilized in the small-scale system) so as to afford in toto the required additional carrier particle surface area for attachment and growth of the increased number of cells, and/or by maintaining the same approximate bed height used in the small-scale experiments but increasing overall volume by increasing the radial dimensions of the bed, thus providing the increased carrier particle surface area needed to accommodate attachment and growth of the increased number of cells. For non-anchorage-dependent cells, the same options are available, with the difference that the overall increase in carrier particles (by increased number of subunits and/or increased radial dimensions) is for the purpose of providing the increased void space in the carrier particle bed(s) needed to entrap the increased number of cells and provide area for growth of those cells.

Although the invention herein has been described with respect to particular features and embodiments, and illustrated with reference to particular drawings, materials of construction and the like, it is to be understood that these are not considered to be limitations of the invention except as otherwise recited in the appended claims.

What is claimed is:

1. An apparatus for culturing animal cells, comprising:
   (a) a vertically-oriented, liquid-tight housing comprising a top, a bottom, and surrounding side walls therebetween;
   (b) within said housing, a first culture subunit comprising a first vertically-oriented receptacle area, having a bottom portion and side walls upstanding therefrom, a first perforated plate constructed and arranged above said bottom portion so as to define a first spent culture fluid collection space, and a first packing of cell carrier particles and animal cells within said first receptacle area supported by said first perforated plate;
   (c) within said housing, a second culture subunit, comprising a second vertically-oriented receptacle area, having a bottom portion and side walls upstanding therefrom, a second perforated plate constructed and arranged above said bottom portion so as to define a second spent culture fluid collection space, and a second packing of cell carrier particles and animal cells within said second receptacle area supported by said second perforated plate, said second culture subunit being disposed vertically above, and spaced vertically apart from, said first culture subunit so as to define a culture fluid flow space therebetween, and wherein the bottom portion and upstanding side walls of at least one of said first and second culture subunits are distinct from, and unaffixed to, said housing, and are sized so as to define a culture fluid flow space between the surrounding side walls of said housing and said upstanding side walls of said first or second culture subunit;

(d) conduit means positioned and arranged for placing the first spent culture fluid collection space of said first culture subunit in liquid communication with the second spend culture fluid collection space of said second culture subunit;

(e) culture medium inlet means positioned and arranged so as to introduce, into said housing, culture medium for separate and parallel introduction into said first receptacle area, said second receptacle area, and said culture fluid flow spaces; and (f) liquid withdrawing means associated at least in part with said conduit means and positioned and arranged so as to withdraw from said housing spent culture fluid from said first and second spent culture fluid collection spaces.

2. An apparatus for culturing animal cells according to claim 1, further comprising, within said housing, one or more additional culture subunits, each comprising a vertically-oriented receptacle area, having a bottom portion and upstanding side walls distinct from and unaffixed to said housing and sized so as to define a culture fluid flow space between the surrounding side walls of said housing and said upstanding side walls of said additional culture subunit, each of said one or more additional culture subunits including a perforated plate constructed and arranged above the bottom portion so as to define a spent culture fluid collection space, and each said receptacle area of each said additional culture subunit containing a packing of cell carrier particles and animal cells therewithin supported on the perforated plate, the vertical disposition of all culture subunits within said housing being spaced apart so as to provide a culture fluid flow space between vertically adjacent culture subunits, and wherein the spent culture fluid collection spaces of all said culture subunits are in liquid communication by said conduit means.

3. An apparatus for culturing animal cells, comprising:

(a) a cylindrical, vertically-oriented, liquid-tight housing comprising a circular housing base and an upstanding side wall extending from the periphery of said housing base;

(b) within said housing, a first culture subunit comprising a first vertically-oriented receptacle area formed from the circular housing base of said housing and a predetermined height of the surrounding side wall of said housing, said first receptacle having arranged at a vertical distance above the circular housing base a planar perforate plate, of substantially the same diameter of said circular housing base, and having a centrally-disposed opening therein, whereby the space between sad circular housing base and said perforate plate defines a first spent culture fluid collection space, said first receptacle further comprising hollow, vertically-oriented liquid conduit means surrounding and upstanding from the centrally-disposed opening in said perforate plate and open at its upper and lower ends, said first receptacle further comprising a first packing of cell carrier particles and animal cells supported by said perforate plate;

(c) within said housing, a second culture subunit at a fixed vertical distance above said first culture subunit and comprising a second cylindrical vertically-oriented receptacle area comprised of elements distinct from and unaffixed to said housing, said second receptacle area comprising a circular base member and an upstanding surrounding side wall extending from the periphery of said base member, the diameter of said second receptacle area begin less than that of the housing such that a annular culture medium flow space is defined between the housing side wall and the side wall of the second receptacle area, the base member of said second receptacle having an opening centrally disposed therein and lying above the open upper end of said liquid conduit means, said second receptacle further comprising a planar perforate plate of substantially the same diameter of the circular base member of the second receptacle area, arranged at a vertical distance above said circular base member of said second receptacle area, whereby the space between said circular base member and said perforate plate of said second receptacle area defines a second spent culture fluid collection space, and whereby said second spent culture fluid collection space is in liquid communication with said first spent culture fluid collection space by said liquid conduit means, said second receptacle further comprising a second packing of cell carrier particles and animal cells supported by said perforate plate of said second receptacle, and wherein the base member of said second receptacle is vertically disposed a predetermined distance above the first receptacle area so as to define a culture medium flow space therebetween;

(d) culture medium inlet means positioned and arranged so as to introduce, into said housing, culture medium for separate and parallel introduction into said second receptacle area, said culture medium flow space and said first receptacle area; and (e) liquid withdrawing means, comprising at least in part said liquid conduit means, for withdrawing from said housing spent culture fluid from said first and second spent culture fluid collection spaces.

* * * * *